(12) United States Patent
Yamashita et al.

(10) Patent No.: US 10,866,240 B2
(45) Date of Patent: Dec. 15, 2020

(54) METHOD FOR ANALYZING PSA AND METHOD FOR DISTINGUISHING PROSTATE CANCER FROM PROSTATIC HYPERTROPHY USING THAT METHOD FOR ANALYZING PSA

(75) Inventors: Katsuko Yamashita, Kanagawa (JP); Keiko Fukushima, Kanagawa (JP); Shiro Baba, Kanagawa (JP); Takefumi Satoh, Kanagawa (JP)

(73) Assignee: KONICA MINOLTA, INC., Tokyo (JP)

( * ) Notice: Subject to any disclaimer, the term of this patent is extended or adjusted under 35 U.S.C. 154(b) by 1088 days.

(21) Appl. No.: 13/147,905

(22) PCT Filed: Feb. 4, 2010

(86) PCT No.: PCT/JP2010/051622
§ 371 (c)(1),
(2), (4) Date: Aug. 4, 2011

(87) PCT Pub. No.: WO2010/090264
PCT Pub. Date: Aug. 12, 2010

(65) Prior Publication Data
US 2011/0294141 A1   Dec. 1, 2011

(30) Foreign Application Priority Data

Feb. 4, 2009  (JP) ................................. 2009-023597

(51) Int. Cl.
*G01N 33/574* (2006.01)
(52) U.S. Cl.
CPC ............... *G01N 33/57434* (2013.01); *G01N 2333/4724* (2013.01); *G01N 2800/342* (2013.01)

(58) Field of Classification Search
CPC .. G01N 1/00; G01N 33/574; G01N 33/57407; G01N 33/57434; G01N 2203/00; G01N 2400/00; G01N 2800/00; G01N 2800/342; G01N 2001/00
See application file for complete search history.

(56) References Cited

U.S. PATENT DOCUMENTS

| 2004/0014033 A1 | 7/2004 | Shriver et al. | |
| 2009/0023220 A1 | 1/2009 | Junko et al. | |
| 2011/0236995 A1* | 9/2011 | Hirano et al. | 436/501 |
| 2011/0294141 A1 | 12/2011 | Yamashita et al. | |

FOREIGN PATENT DOCUMENTS

| CN | 101213454 A | 7/2008 |
| GB | 2 361 060 A | 10/2001 |
| GB | 2 379 444 A | 3/2003 |
| JP | 2002-55108 A | 2/2002 |
| JP | 2006-515927 A | 6/2006 |
| WO | 2004066808 A2 | 8/2004 |
| WO | 2006/125580 A1 | 11/2006 |

OTHER PUBLICATIONS

Invitrogen catalog (pp. 1-3, Dec. 15, 2006).*
Arenas et al. (Glycoconjugate Journal 16(7): 375-382, Jul. 1999).*
Arenas et al., "A lectin histochemistry comparative study in human normal prostate, benign prostatic hyperplasia, and prostatic carcinoma," Glycoconjugate Journal, vol. 16, No. 7, Jul. 1, 1999 (Jul. 1, 1999), pp. 375-382.
Fukushima et al., "1,2-Fucosylated and—N-acetylgalactosaminylated prostate-specific antigen as an efficient marker of prostatic cancer," Glycobiology, vol. 20, No. 4, Apr. 1, 2010 (Apr. 1, 2010 ), pp. 452-460.
McMahon et al., "Evaluation of Three Techniques for Differential Diagnosis of Prostatic Needle Biopsy Specimens," Journal of Clinical Pathology, BMJ Publishing Group, GB, vol. 45, No. 12, Jan. 1, 1992 (Jan. 1, 1992 ), pp. 1094-1098.
Supplementary European Search Report, dated Sep. 6, 2012, EP application No. 10738595.7, 5 pages.
Chinese Journal of Andrology, 2008, vol. 22, No. 6, DuGuang et al.
Peracaula, et al.; Altered glycosylation pattern allows the distinction between prostate-specific antigen (PSA) from normal and tumor origins; Glycobiology; 2003; 457-470; vol. 13, No. 6.
Ohyama, et al.; Carbohydrate structure and differential binding of prostate specific antigen to *Maackia amurensis* lectin between prostate cancer and benign prostate hypertrophy; Glycobiology; 2004; 671-679; vol. 14, No. 8.

(Continued)

*Primary Examiner* — Alana Harris Dent
(74) *Attorney, Agent, or Firm* — Kilpatrick Townsend & Stockton LLP

(57) ABSTRACT

A method for distinguishing prostate cancer from prostatic hypertrophy using the method for analyzing PSA and an analysis kit of PSA are provided. An object of the present invention can be solved by being brought into contact a lectin having an affinity for p-N-acetylgalactosamine residues and/or a lectin having an affinity for fucose a(I, 2) galactose residues with a sample possibly containing PSA, to determine an amount of PSA having an affinity for the lectin. A method for distinguishing prostate cancer from prostatic hypertrophy can be provided by this method.

4 Claims, 2 Drawing Sheets

(56) References Cited

OTHER PUBLICATIONS

Tajri et al.; Oligosaccharide profiles of the prostate specific antigen in free and complexed forms from the prostate cancer patient serum and in seminal plasma: a glycopeptide approach; Glycobiology; 2-8; vol. 18, No. 1, Jan 2008.

Yamashita, et al.; Purification and Characterization of a Fucα1→2Galβ1→ and GalNAcβ1→specific Lectin in Root Tubers of *Trichosanthese japonica*; J. Biol. Chem.; 1992; 25414-25422; vol. 267, No. 35.

Tabares, et al.; Different glycan structures in prostate-specific antigen from prostate cancer sera in relation to seminal plasma PSA; Glycobiology; 2006; 132-145; vol. 16, No. 2.

Oyama; "Zenritsusen Gan Screening no Atarashii Tenkai Gan Tokuiteki PS Awa Sonzai Suruka?: PSA no Tosa Kozo Kaiseki kara;" Urology View; 2005; 77-82; vol. 3, No. 4.

Yamashita, et al.; Expression of Siaα2→6Galβ1→4GlcNAc Residues on Sugar Chains of Glycoproteins Including Carcinoembryonic Antigens in Human Colon Adenocarcinoma: Applications of *Trichosanthes japonica* Agglutinin I for Early Diagnosis; Cancer Res.; 1995; 1675-1679; vol. 55.

Fukushima, et al.; Elevation of α2→6 Sialytransferase and α1→2 Fucosyltransferase Activities in Human Choriocarcinoma; 1998; 4301-4306; vol. 58.

Fukushima, et al.; Elevated Serum Levels of *Trichosanthese japonica* Agglutinin-I Binding Alkaline Phosphatase in Relation to High-Risk Groups for Hepatocellular Carcinomas; Clin. Cancer Res.; 1998; 2771-2777; vol. 4.

Fukushima et al., "Carbohydrate structural changes of prostate specific antigen between prostate cancer and benign prostate hypertrophy," 29th Japan Society for Molecular Tumor Marker Research Program Compendium, 2009, pp. 84-85.

Gotoh et al., "Molecular cloning and characterization of beta1,4-N-acetylgalactosaminyltransferases IV synthesizing N,N'-diacetyllactosediamine," FEBS Letters, 2004, vol. 562(1-3), pp. 134-140.

Mollicone et al., "Molecular genetics of alpha-L-fucosyltransferase genes (H, Se, Le, FUT4, FUT5 and FUT6)," Transfus. Clin. Biol., 1994, vol. 1(2), pp. 91-97.

\* cited by examiner

METHOD FOR ANALYZING PSA AND METHOD FOR DISTINGUISHING PROSTATE CANCER FROM PROSTATIC HYPERTROPHY USING THAT METHOD FOR ANALYZING PSA

CROSS-REFERENCE TO RELATED APPLICATIONS

The present application is a National Stage application under 35 U.S.C. § 371, claiming priority to PCT/JP10/051622, filed Feb. 4, 2010, which application claims the benefit of priority to Japanese Patent Application No. 2009-023597, filed Feb. 4, 2009, the teachings of which are incorporated herein by reference in their entirety for all purposes.

TECHNICAL FIELD

The present invention relates to: a method for analyzing PSA (Prostate Specific Antigen), a method for distinguishing prostate cancer from prostatic hypertrophy using that method for analyzing PSA, and an analysis kit for PSA. According to the present invention, prostate cancer and prostatic hypertrophy can be clearly distinguished using a lectin which binds to the carbohydrate chain specifically expressed in PSA secreted by cancer cells of prostate cancer.

BACKGROUND ART

Prostate cancer is mainly developed in men aged 60 years and older. Prostate cancer has become the second leading cause of cancer-related death, after lung cancer, for men in America and Europe. The incidence of prostate cancer has increased since 1975, and one of the reasons for this is the spread of diagnosis using the measurement of the prostate specific antigen (hereinafter referred to as PSA). Early cancer which is difficult to detect by a conventional digital rectal examination has been found by the measurement of PSA.

PSA is a protein secreted in a glandular cavity of the prostate by glandular cells of the prostate. PSA is expressed in the prostate tissue-specifically, but not cancer-specifically. Thus, it is known that PSA is increased in benign diseases, such as prostatic hypertrophy and prostatitis, other than prostate cancer.

At present, the PSA assay widely used is total PSA assay wherein both complexed PSA, in which PSA bound to α1-antichymotrypsin (hereinafter sometimes referred to as PSA-ACT), and free PSA can be measured. When the measured value of total PSA of a subject is 10 ng/mL or more, the probability of prostate cancer is 50% or more in the subject. Twenty five percent of patients exhibiting a total PSA value of 4-10 ng/mL are prostate cancer patients, and 15% of patients exhibiting a total PSA value of 2-4 ng/mL are prostate cancer patients. The range of 4-10 ng/mL of total PSA is referred to as the gray zone. Even in the case of patients having prostatic hypertrophy, there are many patients exhibiting a total PSA value in the gray zone. For this reason, the development of a method of analyzing PSA, which can distinguish between prostate cancer patients and prostatic hypertrophy patients, is desired.

The ratio of free PSA to total PSA is measured in order to distinguish prostate cancer from prostatic hypertrophy in patients exhibiting total PSA values in the gray zone. It has been reported that the ratios of free PSA to total PSA in sera of prostate cancer patients is lower than that in normal sera. The free PSA value is measured by the ELISA method for free PSA. Then the ratio of the free PSA value to the total PSA value (hereinafter sometimes referred to as "free/total PSA ratio") is calculated. When the value of the free/total PSA ratio is not more than 25%, there exist tumors in the prostate at the high frequency. However, in samples in the gray zone, the probability of prostate cancer is 56% in cases having a free/total PSA ratio of 0 to 10%, the probability of prostate cancer is 28% in cases having a free/total PSA ratio of 10-15%, the probability of a prostate cancer is 20% in cases having a free/total PSA ratio of 15-20%, and the probability of a prostate cancer is 16% in cases having a free/total PSA ratio of 20-25%. Thus, even if the free/total PSA ratio is used, it is not easy to distinguish prostate cancer from prostatic hypertrophy.

In the case of patients exhibiting more than 10 ng/mL of total PSA and patients exhibiting 4-10 ng/mL (gray zone) of total PSA and not more than 25% in a free PSA/total PSA ratio, a biopsy of prostate grand is performed for a definitive diagnosis of prostate cancer. However, in the latter patients, prostate cancer is detected around 30% of the time. Therefore, an excessive burden is placed on the patient. For this reason, the development of a method for simply and easily distinguishing prostate cancer from prostatic hypertrophy has been desired.

It is known that PSA is a glycoprotein having one asparagine-linked carbohydrate chain (hereinafter referred to as an N-glycan chain), and PSA from prostate cancer patients has a higher-branched complex type of N-glycans. Further, it has been considered that PSA of prostate cancer patients might have a cancer-specific carbohydrate chain. For example, an N-glycan chain of PSA secreted from LNCaP cells derived from a prostate cancer was analyzed by using a mass spectrometer. As a result, it was reported that the N-glycan chain has a high content of N-acetylhexosamine (HexNAc) and fucose, and less sialic acids compared to an N-glycan chain in PSA of normal seminal fluid (non-patent document 1). However, the sugar chain structure of PSA from the LNCaP cells is different from that in serum PSA in prostate cancer patients, because the carbohydrate chain in PSA of the LNCaP cells contains fewer sialic acid residues. Therefore, the characteristics of PSA from LNCaP cells were not considered to be the same as those of PSA from prostate cancer patients.

Also, Oyama et al. found that N-glycans of PSA in the prostate cancer patient serum contained sialic acid α(2, 3) galactose residues (Sialic acid α2,3 Gal-R), and that more sialic acid α(2, 3) galactose residues were linked to PSA of prostate cancer patient serum compared to PSA of prostatic hypertrophy patient serum (patent Reference 1 and non-patent Reference 2). Further, a method for distinguishing prostate cancer from prostatic hypertrophy has been developed by binding PSA from the prostate cancer patient serum to *Maackia amurensis* agglutinin (hereinafter referred to as MAA) which can specifically bind to the sialic acid α(2, 3) galactose residues, and measuring the ratio of MAA-bound PSA to total PSA (patent reference 1 and non-patent reference 2). However, besides PSA, α1-antichymotrypsin also has the sialic acid α(2, 3) galactose residues, and therefore α1-antichymotrypsin can also bind to MAA. Thus, in the case of the PSA bound to α1-antichymotrypsin, i.e. PSA-ACT, PSA having sialic acid α(2, 3) galactose residues cannot be separated from PSA lacking sialic acid α(2, 3) galactose residues. Thus, it is necessary to measure free PSA in order to distinguish a prostate cancer patient from a prostatic hypertrophy patient.

Tajiri et al. have compared the sugar chain structures of PSA from two prostate cancer patient sera to that of PSA in normal seminal fluid using mass spectrometry. It has been reported that PSA of the prostate cancer patient serum is sialylated and fucosylated (non-patent reference 3). However, it has not been reported that a prostate cancer patient can be distinguished from a prostatic hypertrophy patient by the analysis of carbohydrate chains other than the sialic acid α(2, 3) galactose residues.

CITATION LIST

Patent Literature

[Patent literature 1] Japanese Unexamined Patent Publication (Kokai) No. 2002-55108

Non-Patent Literature

[Non-patent literature 1] Glycobiology, 2003, (the United state), vol. 13, p. 457-470
[Non-patent literature 2] Glycobiology, 2004, (the United state), vol. 14, p. 671-679
[Non-patent literature 3] Glycobiology, 2008, (the United state), vol. 18, p. 2-8

SUMMARY OF INVENTION

Technical Problem

The present inventors have attempted to distinguish PSA of normal person from PSA of prostate cancer patients by using a lectin-immobilized column, i.e. MAA described in patent reference 1, and measuring PSA bound to MAA columns. However, when PSA was separated by using an MAA column, the recovery rate of normal PSA which does not have sialic acid α(2, 3) galactose residues was 70%. Therefore, this result indicated that PSA nonspecifically bound to the MAA column. Also, the recovery rate of PSA from prostate cancer patient serum was 40%, suggesting that PSA having sialic acid α(2, 3) galactose residues was not eluted with 0.4M lactose from the MAA column in addition to nonspecific binding of the MAA column. These results indicated that the amount of PSA having sialic acid α(2, 3) galactose residues cannot be accurately measured using a MAA column.

At present, not less than 100 kinds of lectin are commercially available. The present inventors have carried out research on the determination of the carbohydrate structures expressed on PSA from prostate cancer patient serum using combinations of various plant lectins having different carbohydrate binding abilities, and then have conducted intensive studies into a method for distinguishing between PSA of prostate cancer and PSA of prostatic hypertrophy. As a consequence, the present inventors have found that in the blood of a prostate cancer patient, there exists PSA having an affinity for *Trichosanthes japonica* agglutinin-II (hereinafter sometimes referred to as TJA-II) or *Wisteria floribunda* agglutinin (hereinafter sometimes referred to as WFA). The present inventors have also been able to distinguish between PSA from prostate cancer patient serum and PSA from prostatic hypertrophy patient serum by using TJA-II or WFA. More particularly, the present inventors found that serum PSA from most prostate cancer patients has β-N-acetylgalactosamine residues (GalNAcβ1→R) and/or fucose α(1, 2) galactose residues (Fucα1→2Galβ1→R).

The present invention is based on the above findings.

Solution to Problem

The present invention relates to a method for analyzing PSA characterized in that a lectin having an affinity for β-N-acetylgalactosamine residues is brought into contact with a sample possibly containing PSA, to determine an amount of PSA having an affinity for the lectin.

The method for analyzing PSA according to a preferable embodiment of the present invention comprises the steps of (a) bringing the lectin having an affinity for a β-N-acetylgalactosamine residue into contact with the sample possibly containing PSA, to separate PSA having an affinity for the lectin from PSA lacking an affinity for the lectin; and (b) determining the amount of PSA having an affinity for the lectin.

According to a preferable embodiment of the method for analyzing PSA of the present invention, the amount of PSA having an affinity for the lectin is determined (1) by measuring an amount of separated PSA having an affinity for the lectin, (2) by measuring an amount of PSA in a sample before the separation and an amount of the separated PSA having an affinity for the lectin, or (3) by measuring an amount of PSA in a sample before the separation and an amount of the separated PSA lacking an affinity for the lectin.

According to a preferable embodiment of the method for analyzing PSA of the present invention, the amount of PSA is determined by measuring total PSA or free PSA.

According to a preferable embodiment of the method for analyzing PSA of the present invention, the lectin is *Trichosanthes japonica* agglutinin-II or *Wisteria floribunda* agglutinin.

According to another preferable embodiment of the method for analyzing PSA of the present invention, the lectin further has an affinity for fucose α(1, 2) galactose residues.

According to a preferable embodiment of the method for analyzing PSA of the present invention, the sample is obtained from a patient suspected of having prostate cancer.

A method for analyzing PSA according to a preferable embodiment of the present invention is for diagnosis of prostate cancer.

The present invention relates to a method for analyzing PSA, characterized in that a lectin having an affinity for fucose α(1, 2) galactose residues is brought into contact with a sample possibly containing PSA, to determine an amount of PSA having an affinity for the lectin.

According to another preferable embodiment of the method for analyzing PSA of the present invention, the method for analyzing PSA comprises the steps of (a) bringing into contact the lectin having an affinity for fucose α(1, 2) galactose residues with the sample possibly containing PSA, to separate PSA having an affinity for the lectin from PSA lacking an affinity for the lectin; and (b) determining the amount of PSA having an affinity for the lectin.

According to a preferable embodiment of the method for analyzing PSA of the present invention, the amount of PSA having an affinity for the lectin is determined (1) by measuring an amount of separated PSA having an affinity for the lectin, (2) by measuring an amount of PSA in a sample before the separation and an amount of the separated PSA having an affinity for the lectin, or (3) by measuring an amount of PSA in a sample before the separation and an amount of the separated PSA lacking an affinity for the lectin.

According to a preferable embodiment of the method for analyzing PSA of the present invention, the amount of PSA is determined by measuring total PSA or free PSA.

According to a preferable embodiment of the method for analyzing PSA of the present invention, the lectin is *Trichosanthes japonica* agglutinin-II or *Wisteria floribunda* agglutinin.

According to a preferable embodiment of the method for analyzing PSA of the present invention, the sample is obtained from a patient suspected of having prostate cancer.

A method for analyzing PSA according to a preferable embodiment of the present invention is for diagnosis of prostate cancer.

The present invention relates to a method for analyzing PSA, characterized in that a lectin having an affinity for β-N-acetylgalactosamine residues and a lectin having an affinity for fucose α(1, 2) galactose residues are brought into contact with a sample possibly containing PSA, to determine an amount of PSA having an affinity for the lectins.

According to another preferable embodiment of the method for analyzing PSA of the present invention, the method for analyzing PSA comprises the steps of (a) bringing the lectin having an affinity for β-N-acetylgalactosamine residues and the lectin having an affinity for fucose α(1, 2) galactose residues into contact with the sample possibly containing PSA, to separate PSA having an affinity for the lectins from PSA lacking an affinity for the lectins; and (b) determining the amount of PSA having an affinity for the lectins.

According to a preferable embodiment of the method for analyzing PSA of the present invention, the amount of PSA having an affinity for the lectin is determined (1) by measuring an amount of separated PSA having an affinity for the lectin, (2) by measuring an amount of PSA in a sample before the separation and an amount of the separated PSA having an affinity for the lectin, or (3) by measuring an amount of PSA in a sample before the separation and an amount of the separated PSA lacking an affinity for the lectin.

According to a preferable embodiment of the method for analyzing PSA of the present invention, the amount of PSA is determined by measuring total PSA or free PSA.

According to a preferable embodiment of the method for analyzing PSA of the present invention, the lectin having an affinity for β-N-acetylgalactosamine residues is *Trichosanthes japonica* agglutinin-II or *Wisteria floribunda* agglutinin, and the lectin having an affinity for fucose α(1, 2) galactose residues is *Trichosanthes japonica* agglutinin-II or *Ulex europaeus* agglutinin-1.

According to a preferable embodiment of the method for analyzing PSA of the present invention, the sample is obtained from a patient suspected of having prostate cancer.

A method for analyzing PSA according to a preferable embodiment of the present invention is for diagnosis of prostate cancer.

Further, the present invention relates to a method for distinguishing prostate cancer from prostatic hypertrophy, characterized in that the amount of PSA having an affinity for the lectin in a sample is analyzed by the above method for analyzing PSA.

Further, the present invention relates to an analysis kit of PSA, comprising a lectin having an affinity for β-N-acetylgalactosamine residues.

According to a preferable embodiment of the analysis kit of PSA of the present invention, the analysis kit of PSA further comprises an anti-PSA antibody.

According to a preferable embodiment of the analysis kit of PSA of the present invention, the lectin is *Trichosanthes japonica* agglutinin-II or *Wisteria floribunda* agglutinin.

According to a preferable embodiment of the analysis kit of PSA of the present invention, the lectin further has an affinity for fucose α(1, 2) galactose residues.

The present invention relates to an analysis kit of PSA, comprising a lectin having an affinity for fucose α(1, 2) galactose residues.

According to a preferable embodiment of the analysis kit of PSA of the present invention, the analysis kit of PSA comprises a lectin having an affinity for β-N-acetylgalactosamine residues, and a lectin having an affinity for fucose α(1, 2) galactose residues.

Advantageous Effects of Invention

According to the method for analyzing PSA, the method for distinguishing prostate cancer from prostatic hypertrophy and the analysis kit of PSA, prostate cancer can be clearly distinguished from prostatic hypertrophy. Further, TJA-II, WFA, and UEA-I can be used in the present invention, and the PSA bound to the lectins can be recovered at a recovery rate of about 100%. Therefore, a quantity of PSA from prostate cancer patient serum having β-N-acetylgalactosamine residues can be measured precisely. Furthermore, TJA-II, WFA and UEA-I columns are reproducible, and reusable.

DESCRIPTION OF EMBODIMENTS

[1] A Method for Analyzing PSA

Figure 1:
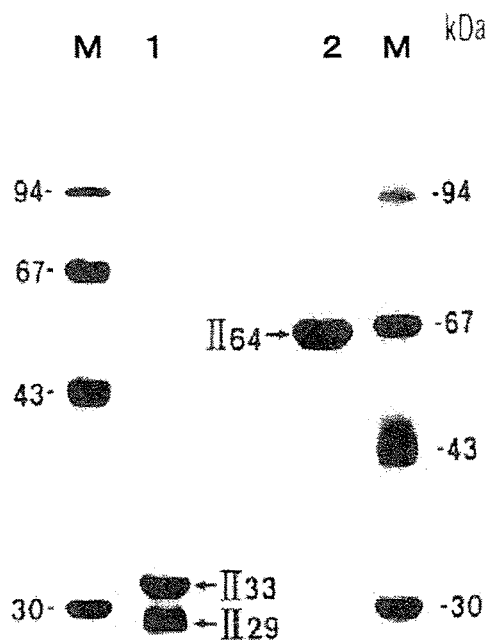
FIG. 1 is a photograph showing the results obtained by electrophoresing a purified TJA-II. M shows a molecular weight marker. Lane 1 shows reduced TJA-II. Lane 2 shows nonreduced TJA-II.

A method for analyzing PSA of the present invention is characterized in that a lectin having an affinity for β-N-acetylgalactosamine residues is brought into contact with a sample possibly containing PSA, to determine the amount of PSA having an affinity for the lectin.

An example of a lectin which may be used in the present invention is a lectin having an affinity for β-N-acetylgalactosamine residues (GalNAcβ1→R) linked to a nonreducing terminal. In this case, β-N-acetylgalactosamine of a nonreducing terminal must not be substituted by sialic acid and sulfuric acid. The lectin having an affinity for the β-N-acetylgalactosamine residues includes, but is not limited to, TJA-II or WFA.

A further example of a lectin which may be used in the present invention is a lectin having an affinity for fucose α(1, 2) galactose residues (Fucα1→2Galβ1→R). The fucose α(1, 2) galactose residue is a terminal carbohydrate chain having a structure wherein α-fucose is bound to galactose at the C-2 position. The lectin having an affinity for the fucose α(1, 2) galactose residues includes, but is not limited to, UEA-I or TJA-II.

A further example of a lectin which may be used in the present invention is a lectin having an affinity for β-N-acetylgalactosamine residues (GalNAcβ1→R) and fucose α(1, 2) galactose residues bound to a nonreducing terminal. Among the PSA of a prostate cancer patients, there may exist PSA expressing β-N-acetylgalactosamine residues only or PSA expressing fucose α(1, 2) galactose residues only. Furthermore, there is a high possibility that PSA in a prostate cancer patient expresses dominantly either β-N-acetylgalactosamine residues or fucose α(1, 2) galactose residues. Therefore, in the method for analyzing PSA according to the present invention, the lectin having an affinity for β-N-acetylgalactosamine residues (GalNAcβ1→R) bound to a nonreducing terminal and fucose α(1, 2) galactose residues bound to a nonreducing terminal is preferably used. The lectin having an affinity for β-N-acetylgalactosamine residues (GalNAcβ1→R) and fucose α(1, 2) galactose residues bound to the nonreducing terminal includes, but is not limited to, TJA-II.

TJA-II is extracted from a tuberous root of *Trichosanthes japonica* and purified. The molecular weight determined by electrophoresis in the non-reduced condition is 64 kDa. The molecular weight by electrophoresis in the reduced condition is 32 kDa and 29 kDa because TJA-II is dimer having disulfide bond. TJA-II exhibits a strong affinity for β-N-acetylgalactosamine residues (GalNAcβ1→R) and fucose α(1, 2) galactose residues (Fucα1→2Galβ1→R).

WFA is extracted from seeds of *Wisteria floribunda* and purified. WFA exhibits a strong affinity for β-N-acetylgalactosamine residues (GalNAcβ1→R) to itself. Further, WFA also exhibits a strong affinity for a GalNAcβ1→4Gal residue and a GalNAcβ1→4GlcNAc residue.

UEA-I (*Ulex europaeus* agglutinin-1) is a lectin prepared from *Ulex europaeus*, and the molecular weight is approximately 26,700 Da. UEA-I has a carbohydrate binding specificity against α-L-Fuc and exhibits a strong affinity for fucose α(1, 2) galactose residues (Fucα1→2Galβ1→4GlcNAc→R).

In the method for analyzing PSA according to the present invention, the lectin having an affinity for β-N-acetylgalactosamine residues, the lectin having an affinity for fucose α(1, 2) galactose residues, and the lectin having an affinity for both β-N-acetylgalactosamine residues and fucose α(1, 2) galactose residues may be used alone or in combinations of two or more.

As the lectin used in the present invention, a commercially available lectin can be used, and further a lectin purified in accordance with conventional methods can also be used. A plant body, such as leaf, stem, flower, root, seed, or the like is scrapped, crushed, and dissolved in a buffer solution. A supernatant is collected by centrifugal separation, and then a lectin can be purified from the supernatant using ammonium sulfate precipitation, ion-exchange column chromatography, hydrophobic column chromatography, gel filtration column chromatography, affinity column chromatography, dialysis, lyophilization, or the like. Particularly, TJA-II can be purified in accordance with the report of Yamashita et al. (Yamashita et al., J. Biol. Chem., 267, 25441-25422, 1992). Further, WFA can be purified in accordance with the report of Toyoshima et al. (Toyoshima et al., Biochemistry, 10, 4457-4463, 1971). Furthermore, UEA-I can be purified in accordance with the report of Hindsgaul et al. (Hindsgaul et al., Carbohydr. Res., 109, 109-142, 1982).

The method for analyzing PSA described herein is not particularly limited, so long as the lectin is brought into contact with a sample possibly containing PSA, to determine the amount of PSA having an affinity for the lectin. Examples of the method for analyzing PSA include (A) a method for separating PSA having an affinity for the lectin from PSA lacking an affinity for the lectin to determine the amount of PSA having an affinity for the lectin (hereinafter sometimes referred to as an analytical method (A)) and (B) a method for determining the amount of PSA having an affinity for the lectin on the condition that the lectin is bound to PSA having an affinity for the lectin (hereinafter sometimes referred to as an analytical method (B)).

Analytical Method (A)

The analytical method (A) comprises (a) a step of bringing a lectin having an affinity for β-N-acetylgalactosamine residues (as a lectin used in the present invention) into contact with a sample possibly containing PSA, to separate PSA having an affinity for the lectin from PSA lacking an affinity for the lectin (hereinafter sometimes referred to as the separation step (a)), and (b) a step of determining the amount of PSA having an affinity for the lectin in the sample (hereinafter sometimes referred to as the determination step (b)).

The method of separating PSA having an affinity for the lectin from PSA lacking an affinity for the lectin in separation step (a) is not particularly limited as long as it is a method utilizing an affinity of PSA for the lectin. For example, the method may be performed by binding a lectin to a carrier (hereinafter, sometimes referred to as a "lectin affinity column"), bringing the carrier into contact with a sample possibly containing PSA, and separating PSA bound to the lectin from PSA not bound to the lectin.

The carrier is not limited as long as it can be bound to a lectin. Examples of the carrier include sepharose, cellulose, agarose, dextran, polyacrylate, polystyrene, polyacrylamide, polymethacrylamide, copolymer of styrene and divinylbenzene, polyamide, polyester, polycarbonate, polyethyleneoxide, hydroxypropyl methylcellulose, polyvinyl chloride, polymethylacrylate, copolymer of polystyrene and polystyrene, polyvinyl alcohol, polyacrylic acid, collagen, calcium alginate, latex, polysulfone, silica, zirconia, alumina, titania and ceramics. The form of the carrier is not also particularly limited, but includes particulate bead, microtiter plate, gel and the like. For example, if a lectin affinity column is used in separation of PSA having an affinity for a lectin from PSA lacking an affinity for a lectin, the carrier preferably has the gel form.

The lectin affinity column may be prepared according to standard procedures. For example, the lectin column may be prepared by performing coupling using CNBr-activated Sepharose 4B according to the protocol recommended by the manufacturer. The binding amount of the lectin to the sepharose gel is preferably from 2 mg/mL to 10 mg/mL.

The method of separating PSA having an affinity for the lectin from PSA lacking an affinity for the lectin using the lectin affinity column may be performed according to a conventional method of separating glycoprotein using lectin affinity columns.

The lectin affinity column is equilibrated with a buffer before applying a sample possibly containing PSA. Examples of the equilibration buffer include a phosphate buffer containing 0.1% bovine serum albumin (BSA), and a Tris-HCl buffer containing 0.1% BSA.

After equilibration of the column, a sample possibly containing PSA is added thereto, and allowed to stand for a predetermined time, to bring the lectin and PSA into contact. The contact time is not particularly limited, and may be properly decided according to the kinds of lectin and their PSA affinity. However, considering the binding rate and the efficiency, the contact is usually performed for 15 minutes to 30 minutes.

The temperature where lectin and PSA are brought into contact is not also particularly limited, but may be properly decided according to the kinds of lectin and their affinity with PSA. However, the contact may be performed at 0° C. to 40° C., preferably at 0° C. to 30° C. If the temperature is lower than 0° C., the column may freeze, and if the temperature is higher than 40° C., non-specific binding of a protein lacking an affinity for the lectin may occur. For example, the temperature where TJA-II and PSA are brought into contact is not particularly limited. However, they are brought into contact at preferably from 4° C. to 10° C. In addition, the temperature where WFA and PSA are brought into contact is also not particularly limited. However, they are brought into contact at preferably from 4° C. to 10° C.

Next, the bound molecules having an affinity for the lectin (hereinafter, sometimes referred to as a "the bound molecules") are separated from the non-bound molecules lacking an affinity for the lectin (hereinafter, sometimes referred to as a "the non-bound molecules").

The non-bound molecules can be obtained by adding a washing buffer to a column, and recovered in the passed-through fractions. The washing buffer is not limited as long as it is a buffer that runs off the non-bound molecules without dissociating the binding of the lectin and PSA. For example, the buffer used in the equilibration may be used as the washing buffer. The volume of the washing buffer may be properly decided depending on the kinds of lectin and affinity with PSA. However, the volume is preferably about 3 to 7 times, more preferably about 5 times the volume of the column.

The bound molecules can be obtained by adding an elution buffer to a column, and recovered in the eluted fractions. The elution buffer contains a haptenic sugar, with which PSA bound to a lectin can be eluted from the lectin. The haptenic sugar may be selected properly in accordance with carbohydrate binding specificity of the lectin. If the lectin is TJA-II, lactose and the like may be used as the haptenic sugar. For example, the bound molecules can be recovered using a phosphate buffer containing 10 mM lactose and 0.1% bovine serum albumin (BSA). In addition, if the lectin is WFA, N-acetylgalactosamine (GalNAc) and the like may be used as the haptenic sugar. For example, the bound molecules can be recovered using a phosphate buffer containing 10 mM GalNAc and 0.1% bovine serum albumin (BSA). The volume of the elution buffer may be selected properly, but is preferably about 3 to 7 times, more preferably about 5 times the volume of the column. The temperature of the elution is not also particularly limited. However, the elution may be performed at 0° C. to 40° C., preferably 2 to 25° C., and more preferably 4 to 20° C. If the temperature is lower than 0° C., the column may freeze, and if the temperature is higher than 40° C., non-specific binding of a protein lacking an affinity for a lectin may occur. For example, the temperature which PSA is eluted from TJA-II is not particularly limited. However, the elution is preferably performed at room temperature. In addition, the temperature which PSA is eluted from WFA is not also particularly limited. However, the elution is preferably performed at room temperature.

In the determination step (b), determination of the amount of PSA having an affinity for the lectin includes (1) Determination by measuring the amount of separated PSA having an affinity for the lectin, (2) Determination by measuring the amount of PSA in the sample before the separation, and by measuring the amount of the separated PSA having an affinity for the lectin, or (3) Determination by measuring the amount of PSA in the sample before the separation, and by measuring the amount of the separated PSA lacking an affinity for the lectin.

The determination (1) by measuring the amount of separated PSA having an affinity for the lectin may be performed by measuring the PSA amount in the binding fractions quantitatively or semi-quantitatively. In other words, the determination is performed by measuring the absolute amount of PSA having an affinity for the lectin contained in the blood of a patient.

The determination (2) by measuring the amount of PSA in the sample before the separation, and measuring the amount of the separated PSA having an affinity for the lectin, may be performed by comparing the PSA amount in the sample before the separation (or the total amount of PSA in the binding fractions and the non-binding fractions) with the PSA amount in the binding fractions to the lectin. Specifically, the PSA amount having an affinity for the lectin can be determined by calculating the ratio of the PSA amount in the binding fractions, to the PSA amount in the sample before separation (or the total amount of PSA in the binding fractions and the non-binding fractions), and for example, can be calculated by either of the equations below.

Binding rate of *PSA*=(amount of *PSA* in the binding fraction/total amount of *PSA* in the binding fraction and the *non*-binding fraction)×100%

Binding rate of *PSA*=(amount of *PSA* in the binding fraction/*PSA* amount in the sample before *a* separation)×100%

In addition, the determination (3) by measuring the amount of PSA in the sample before a separation, and measuring the amount of separated PSA lacking an affinity for a lectin, may be performed by comparing the amount of PSA in the sample before a separation (or the total amount of PSA in the binding fractions and the non-binding fractions) with the amount of PSA in the non-binding fractions. Specifically, the amount of PSA having an affinity for the lectin can be determined by subtracting the amount of PSA in the non-binding fractions from the amount of PSA in the sample before separation (or the total of the amount of PSA in the binding fractions and the non-binding fractions). For example, the amount of PSA having an affinity for the lectin can be calculated by any of the equations below.

Amount of *PSA* having an affinity for *a* lectin=amount of *PSA* in the sample before *a* separation−amount of *PSA* in the *non*-binding fraction Amount of *PSA* having an affinity for *a* lectin=total amount of *PSA* in the binding fractions and the *non*-binding fractions−amount of *PSA* in the *non*-binding fractions In the determinations (1) and (2), the amount of PSA bound to a lectin is measured after separating bound PSA from the lectin. However, in the determination (3), which is the determination from the amount of PSA in the sample before a separation and the amount of PSA in the non-binding fractions, the amount of PSA bound to a lectin is not measured, and thus the amount of PSA bound to a lectin may be determined without separating PSA bound to a lectin.

In addition, regarding obtaining the amount of PSA in the binding fractions and non-binding fractions separately, the measurement of the amount of PSA is preferably performed for all of the fractions. However, the fractions containing PSA are preliminarily analyzed and the amount of PSA can be determined by measuring the fractions of interest.

In the determination step (b), the method of measuring PSA in order to determine the amount of PSA having an affinity for a lectin, is not particularly limited as long as it is a method that allows quantitative or semi-quantitative determination of PSA. Examples of the method of measuring PSA include a method of measuring total PSA and a method of measuring free PSA. The method of measuring total PSA or the method of measuring free PSA may be performed by immunological techniques using antibody or a fragment thereof (for example, enzyme immunoassay, latex agglutination immunoassay, chemiluminescent immunoassay, fluorescent antibody method, radioimmunoassay, immunoprecipitation method, immunohistological staining method, or the western blot) according to standard procedures. Commercially available PSA measurement kits may also be used.

In the case where the immunological assay is used as the method of measuring total PSA, a monoclonal antibody or a polyclonal antibody is used that can bind to both PSA-ACT and free PSA. On the other hand, in the case where the immunological assay is used as the method of measuring free PSA, a monoclonal antibody or a polyclonal antibody is used that can bind only to free PSA. The monoclonal antibody or the polyclonal antibody can be prepared by a known method except that PSA-ACT or free PSA is used as an immunizing antigen. For example, the monoclonal antibody can be prepared according to Koehler and Milstein's method (Nature 256: 495-497, 1975). In addition, the polyclonal antibody can be prepared by conventional immunization with an antigen that is PSA-ACT or free PSA as alone or as bound to BSA, KLH and the like, which is mixed with an adjuvant such as simple adjuvant or Freund's complete adjuvant, for example, in the skin of a rabbit. The blood is collected at the time when the antibody titer increases, which may be utilized as it is as an antiserum, or the antibody may be used as purified by a known method.

By the analysis of Examples described below, it was found that the lectin affinity column using TJA-II or WFA, which may be used in the method for analyzing PSA of the present invention, can recover about 100% (at least 97% or more) of PSA in the sample. In comparison to this, with MAA described in Patent Reference 1, the recovery rate was 30 to 70% when using a phosphate buffer containing 0.4M lactose as an eluting solution, and the recovery rate did not improve even if the eluting solution was changed to 0.1 M acetic acid solution.

Analysis Method (B)

The analysis method (B) is a method wherein PSA having an affinity for a lectin is directly detected by the lectin. Specifically, analysis method (B) includes the lectin blot analysis by electrophoresis, or the lectin blot analysis by dot blotting. Any one of the lectin blot analyses may be performed according to standard procedures. With the lectin blot analysis by electrophoresis, a sample possibly containing PSA is subjected to electrophoresis, and PSA is transferred to a nitrocellulose membrane or a PVDF membrane, which is used as a sample membrane. With the lectin blot analysis by dot blotting, a sample possibly containing PSA is adsorbed onto a nitrocellulose membrane or a PVDF membrane by a dot blotting apparatus, and the membrane is used as a sample membrane. Blocking is performed with a blocking buffer for the sample membrane, and the sample membrane is brought into contact with a solution containing a biotin-labeled lectin, for example biotin-labeled WFA or biotin-labeled TJA-II. Then, the sample membrane is brought into contact with avidin labeled with an enzyme such as HRP or ALP, and then brought into contact with solution containing a chromogenic or a luminescent enzyme substrate, and the obtained signal is detected.

Furthermore, method (B) of directly detecting PSA having an affinity for a lectin by the lectin may be performed by the immunoblot analysis and the enzyme immunoassay with partial modification. Specifically, the monoclonal antibody or polyclonal antibody for PSA is immobilized on a nitrocellulose membrane or an ELISA plate, and blocking is performed with a blocking buffer. The sample possibly containing PSA is brought into contact with the nitrocellulose membrane or the ELISA plate, and then, brought into contact with a biotin-labeled lectin, for example biotin-labeled WFA or biotin-labeled TJA-II. Then, the sample is bound to avidin labeled with an enzyme such as HRP or ALP, and then the signal can be detected following incubation with a solution containing a chromogenic or a luminescent enzyme substrate.

Examples of the sample used in the method for analyzing PSA of the present invention include PSA-containing biological samples, or samples derived from human body, and biological samples isolated or derived from the human body possibly containing PSA. Examples of the sample to be tested include urine, blood, serum, plasma, spinal fluid, saliva, cell, tissue or organ, and preparations thereof (for example, a biopsy sample, particularly a prostatic biopsy sample). The sample to be tested is preferably blood, serum, plasma, or a prostatic biopsy sample, particularly preferably blood, serum, or plasma. Blood, serum, or plasma is appropriate as a sample to be tested for detecting the prostate cancer, because PSA having β-N-acetylgalactosamine residues and/or fucose α(1, 2) galactose residues is released into the blood in the initial stage of disease in prostate cancer patients, whereas little PSA having β-N-acetylgalactosamine residues and/or fucose α(1, 2) galactose residues exists in the blood, serum, or plasma of normal healthy subjects and prostatic hypertrophy patients.

A liquid sample such as urine, blood, serum, plasma, spinal fluid and saliva may be used as diluted in the analysis method (A) or the analysis method (B) with an appropriate buffer depending on each of the analysis methods. In addition, a solid sample such as cell, tissue or organ is homogenized with an appropriate buffer in an amount about 2 to 10 times the volume of the solid sample, and a suspension or a supernatant thereof may be used in the analysis method (A) or the analysis method (B) as it is, or after further dilution.

For example, if the lectin affinity column is used in analysis method (A), the liquid sample, or a suspension of the solid sample or a supernatant thereof may be used as diluted with an appropriate buffer. The dilution rate is not particularly limited as long as it does not inhibit the binding of PSA to the lectin. However, the dilution rate is preferably 2 to 400 times, more preferably 2 to 300 times, and most preferably 4 to 200 times. In addition, the volume of the sample applied to the lectin affinity column is preferably equal to or less than 40%, more preferably equal to or less than 30%, and most preferably equal to or less than 20% of the bed volume of the column. For example, if 1 mL bed volume of the lectin affinity column is used, the volume of the sample applied to the lectin affinity column is preferably equal to or less than 400 μL, more preferably equal to or less than 300 μL, and most preferably equal to or less than 200 μL.

[2] Method for Distinguishing Prostate Cancer from Prostatic Hypertrophy

It is possible to distinguish between prostate cancer and prostatic hypertrophy by analyzing the amount of PSA having an affinity for a lectin in a sample by the method for analyzing PSA.

It is possible to determine whether the patient has the prostate cancer or not by measuring the amount of PSA having an affinity for the lectin by the method for analyzing PSA, and comparing that with the amount of PSA having an affinity for the lectin in the blood or the like collected from prostatic hypertrophy patients or normal healthy subjects. More specifically, it is possible to determine that the patient has the prostate cancer if there is significantly more PSA having an affinity for a lectin existing in the sample of the patient than there is in the samples of prostatic hypertrophy patients or normal healthy subjects.

In the analysis method (A), the binding rate to TJA-II, which recognizes β-N-acetylgalactosamine residues and fucose α(1, 2) galactose residues, is different from the binding rate to WFA, which recognizes only β-N-acetylgalactosamine residues. Therefore, it is preferable to decide the cutoff values that allow distinction between prostate cancer and prostatic hypertrophy by the measurement value of the used lectin. The cutoff value is most preferably a value that allows determination of prostate cancer patients as positive by 100%, and determination of prostatic hypertrophy patients as negative by 100%. If the measurement values are overlapped between the prostate cancer patients and the prostatic hypertrophy patients in accordance with increases of the analyzed population of prostate cancer and prostatic hypertrophy, it is preferable to select a value that allows 100% judgment of the prostate cancer patients as positive as the cutoff value. However, it is also possible to select any value in the overlapped range as the cutoff value. Specifically, if the amount of PSA in the TJA-II binding fraction is measured as described below in examples, the cutoff value for detecting prostate cancer patients is not limited as long as it is a value that allows detection of PSA of the prostate cancer patients, but can be set as, for example, some value between 200 pg/mL and 240 pg/mL, preferably 220 pg/mL.

In addition, the binding rate of PSA to a lectin in Examples described below may be decided from the percentage that can be obtained in the following equation.

Binding rate of PSA=(amount of PSA in the binding fraction/amount of PSA amount in the sample before a separation)×100%

The cutoff value of the binding rate of PSA is also most preferably a value that allows determination of prostate cancer patients as positive by 100%, and determination of prostatic hypertrophy patients as negative by 100%. If the binding rates of PSA to the lectin are overlapped between the prostate cancer patients and the prostatic hypertrophy patients in accordance with increases of the analyzed population of prostate cancer and prostatic hypertrophy, it is preferable to select a value that allows 100% judgment of the prostate cancer patients as positive as the cutoff value. However, it is also possible to select any value in the overlapped range as the cutoff value. Specifically, the cutoff value of the TJA-II binding rate of PSA in Examples described below is not limited as long as it is a value that allows detection of the prostate cancer, but can be set up as, for example, a value between 1.8% and 3%, preferably 2.4%.

[3] Diagnosis Kit for Prostate Cancer

The diagnosis kit of the present invention contains a lectin having an affinity for β-N-acetylgalactosamine residues. In addition, the diagnosis kit of the present invention may also contain a lectin having an affinity for fucose α(1, 2) galactose residues. The diagnosis kit of the present invention may contain a lectin having an affinity for β-N-acetylgalactosamine residues (GalNAcβ1→R) and fucose α(1, 2) galactose residues. The lectin contained in the diagnosis kit of the present invention also includes those bound to the above-mentioned carriers.

The diagnosis kit of the present invention may contain a lectin having an affinity for β-N-acetylgalactosamine residues, a lectin having an affinity for fucose α(1, 2) galactose residues, or a lectin having an affinity for β-N-acetylgalactosamine residues and fucose α(1, 2) galactose residues, alone or in a combination of two or more.

The lectin having an affinity for β-N-acetylgalactosamine residues is not particularly limited, but includes TJA-II or WFA. In addition, the lectin having an affinity for fucose α(1, 2) galactose residues is not particularly limited, but includes UEA-1 or TJA-II. Furthermore, the lectin having an affinity for β-N-acetylgalactosamine residues (GalNAcβ1→R) and fucose α(1, 2) galactose residues includes TJA-II.

The diagnosis kit of the present invention may further contain an anti-PSA antibody (for example, antibody specifically binding to PSA-ACT or free PSA) or a fragment thereof. As the antibody, any of monoclonal antibody or polyclonal antibody may be used. The antibody fragment is not particularly limited as long as it has specific binding ability to PSA-ACT or free PSA, and appropriate fragments include, for example, Fab, Fab', F(ab')$_2$, or Fv.

The diagnosis kit of the present invention containing the lectin and the anti-PSA antibody, may contain the anti-PSA antibody or a fragment thereof in a desired form depending on the immunological technique used.

For example, in a case where an immunological technique using a labeled antibody is used such as enzyme immunoassay detected by fluorescence, chemiluminescence, or radioactivity, the diagnosis kit may contain the anti-PSA antibody or a fragment thereof in a form of a antibody or a antibody fragment conjugated with a labeling substance. Specific examples of the labeling substance include enzymes such as peroxidase (HRP), alkaline phosphatase (ALP), β-D-galactosidase or glucose oxidase, fluorescent substances such as fluorescein isothiocyanate or rare-earth metal chelate, radioactive isotopes such as $^3$H, $^{14}$C or $^{125}$I, and miscellaneously, biotin, avidin, and chemiluminescent substances. In the case where the antibodies labeled with enzymes such as HRP, ALP or the like is used, they preferably contain an appropriately selected substrate and the like since they cannot generate measurable signal by themselves.

Function

For patients exhibiting a gray PSA value (the total PSA value is 4 to 10 ng/mL), measurement of the free PSA/total PSA ratio (F/T value) of the serum sample is performed as described above. As shown in Table 1, the F/T value is equal to or less than 25% in 7 out of 9 of the prostatic hypertrophy patients. The seven patients are subject to a biopsy to confirm the diagnosis, but in fact, they have prostatic hypertrophy, and thus such biopsy for confirmed diagnosis is excessive burden to the patients.

TJA-II, which may be used in the present invention is a lectin that recognizes fucose α(1, 2) galactose residues and β-N-acetylgalactosamine residues existing at the non-reducing terminal of the sugar chain. WFA is a lectin that recognizes β-N-acetylgalactosamine residues existing at the non-reducing terminal of the sugar chain. UEA-I is a lectin that recognizes fucose α(1, 2) galactose residues existing at the non-reducing terminal of the sugar chain. It is shown for the first time by the present specification that PSA which can bind to TJA-II, WFA or UEA-I exists in the body of the prostate cancer patient, i.e., these sugar chain structures appear in PSA with canceration. As described above, it has been reported that PSA of LNCaP cells has a HexNAcβ1-HexNAc residue on the side of the non-reducing terminal. HexNAc includes β-N-acetylgalactosamine (GalNAcβ) and β-N-acetylglucosamine (GlcNAcβ), which are indistinguishable by mass spectrometric analysis since they have the same molecular weight. In addition, PSA secreted from LNCaP cells was considered not to reflect biological PSA of the prostate cancer patient due to the fact that the sugar chain lacks sialic acid residues. Accordingly, in the present specification, it is possible for the first time to identify β-N-acetylgalactosamine residues and fucose α(1, 2) galactose residues at the non-reducing terminal in the serum PSA of a prostate cancer patient by using the TJA-II column, the WFA column or the UEA-I column. It is considered that the change of the sugar chain structure of PSA with canceration, i.e., appearance of a fucose α(1, 2) galactose residue, a β-N-acetylgalactosamine residue and a sialic acid α(2, 6) β-N-acetylgalactosamine residue has a background of the changes of glycosyltransferase activities, which are associated with the sugar chain synthesis by the onset of the prostate cancer.

In addition, as described in Patent Reference 1 and Non-Patent Reference 2, in a case where MAA that specifically recognizes Siaα2-3Galβ1-4GlcNAc residues is used to detect the change of the sugar chain structure in the prostate cancer, a part of the blood PSA exists as PSA-ACT, wherein the PSA is bound to serum α1-antichymotrypsin. Since MAA also binds to α1-antichymotrypsin, PSA-ACT bound to an MAA column, although the PSA does not contain Siaα2-3Galβ1-4GlcNAc residues. Accordingly, if MAA is used in the separation of PSA, it is necessary to measure free PSA.

On the other hand, TJA-II that may be used in the present invention recognizes fucose α(1, 2) galactose residues and/or β-N-acetylgalactosamine residues existing at the non-reducing terminal of the PSA sugar chain, and WFA recognizes β-N-acetylgalactosamine residues existing at the non-reducing terminal of the PSA sugar chain. However, these sugar chain structures are not linked to serum α1-antichymotrypsin, and therefore, they can be quantified using a total PSA measurement kit. The amount of free PSA is generally equal to or less than 20% of the amount of total PSA, and a total PSA measurement kit may be used in the analysis method of the present invention. Therefore, the present invention is more sensitive than the inventions described in Non-Patent Reference 2 and Patent Reference 1.

EXAMPLES

The present invention now will be further illustrated by, but is by no means limited to, the following Examples and Comparative Examples.

Example of TJA-II Purification

TJA-II was purified from 20 g of the tuberous root of *Trichosanthes japonica* as previously reported (Yamashita et al., J. Biol. Chem., 267, 25441-25422, 1992). Specifically, the tuberous root of *Trichosanthes japonica* was finely shredded, and homogenized with 16 mL of 10 mM phosphate buffer (pH 7.4) containing 0.15 M NaCl using a Waring blender. The resultant liquid was centrifuged at 1000 g for 30 minutes, and 35% to 55% saturated ammonium sulfate fraction precipitate of the obtained supernatant was dissolved in water, and dialyzed with distilled water. After lyophilization, 435 mg of the 35% to 55% saturated ammonium sulfate precipitate was dissolved in 6 mL PBS, and was applied to a 10 mL of porcine stomach mucin-Sepharose 4B (10 mg/mL gel) column that was equilibrated with PBS. The column was washed, and then eluted with PBS containing 0.1 M lactose, to obtain TJA-II.

Example of Column Preparation

The TJA-II column was prepared by coupling purified TJA-II respectively to sepharose columns. Specifically, the TJA-II column was prepared using CNBr-Sepharose 4B (manufactured by GE HealthCare) by immobilizing TJA-II to the column in the density of 3 mg per 1 mL gel volume according to the enclosed protocol recommended by the manufacturer.

In addition, the WFA column was prepared using WFA (manufactured by EY Laboratory) and CNBr-Sepharose 4B (manufactured by GE HealthCare) in the same manner.

Example 1

Analysis of PSA Using TJA-II

In this example, the amount of PSA was measured by the method for analyzing PSA of the present invention using the TJA-II column prepared in the example of column preparation, for 15 patients diagnosed as having prostate cancer and 9 patients diagnosed as having prostatic hypertrophy and having 4.0 ng/mL or more of total PSA.

The TJA-II column (1 mL volume) was equilibrated with PBS containing 0.1% bovine serum albumin (BSA) at 4° C. 1 µL to 50 µL of the serum sample was diluted with PBS to the volume of 200 µL, applied to the column, and held for 30 minutes. Then, the column was washed with 5-fold volume of a washing buffer (PBS containing 0.1% BSA), and fractionated to 1 mL for each, to obtain the TJA-II non-bound molecules. The column was stood at room temperature, and then fractionated to 1 mL for each and eluted with 5-fold volume of an eluting buffer (PBS containing 10 mM lactose and 0.1% BSA), to obtain the TJA-II bound molecules. The total amount of PSA was measured using Access Hybritech total PSA (manufactured by Beckman Coulter, Inc.) for the serum sample before a separation by the TJA-II column, the TJA-II non-bound molecules, and the TJA-II bound molecules. The recovery rate of PSA from the TJA-II column was 97% to 100% at any time. The amount of PSA before a separation in the serum sample, the amount of PSA in the TJA-II binding fraction, and TJA-II binding rate of PSA are shown in Table 1. Meanwhile, the TJA-II binding rate was calculated by the following equation.

*TJA-II*binding rate=(amount of *PSA*in the *TJA-II* binding fraction/total amount of *PSA*in the *TJA-II*non-binding fraction and in the *TJA-II*binding fraction)×100%

In addition, the free PSA in the serum sample before a separation was measured using Access Hybritech free PSA (manufactured by Beckman Coulter Inc.). From the amount of total PSA and the amount of free PSA, the ratio of free PSA/total PSA was calculated. The results are shown in Table 1, FIG. 2 and FIG. 3. Meanwhile, the age, the clinical stage and the Gleason score of the cancer patients are shown in Table 2. The clinical stage indicates the progress level of the prostate cancer. In addition, the Gleason score indicates the degree of malignancy of the prostate cancer in 5 steps of the pathological classes. "1" means mildest cancer, and "5" means worst cancer. In many cases, the prostate cancer has different tissues of different degrees of malignancy, and thus the most prevalent tissue and the next most prevalent tissue are added to obtain the score, which is the Gleason score. For example, if the most prevalent tissue is "3" and the next most prevalent tissue is "4", the Gleason score is "3"+"4"="7". When the Gleason score is "6" or less, the cancer is considered to be low-grade cancer in malignancy, "7" to be intermediate-grade cancer in malignancy, and "8" to "10" to be high-grade cancer in malignancy.

Figure 2:
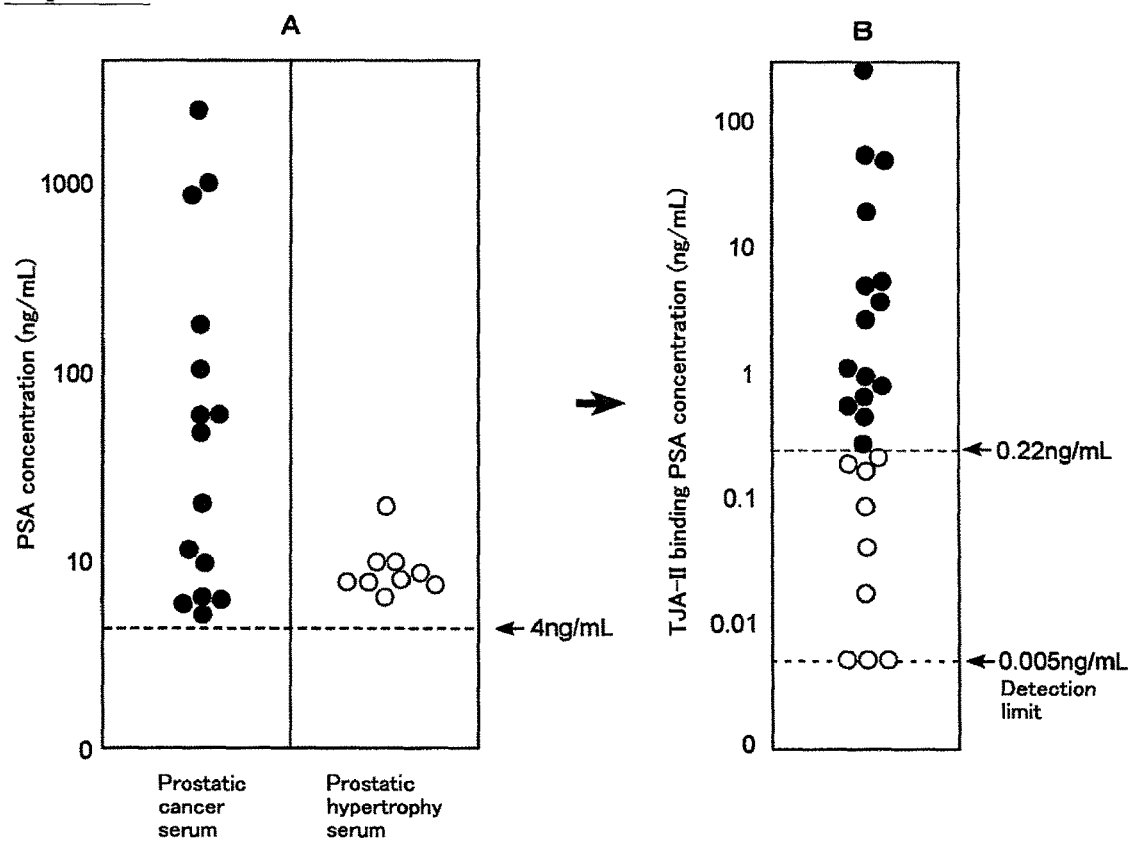
FIG. 2 is a graph showing a quantity of PSA in a serum before the fractionation using a TJA-II column (A) and a quantity of PSA in the TJA-II-bound fractions (B) of a prostate cancer patient and a prostatic hypertrophy patient. A black circle (•) shows a prostate cancer patient. A white circle (○) shows a prostatic hypertrophy patient.
Figure 3:
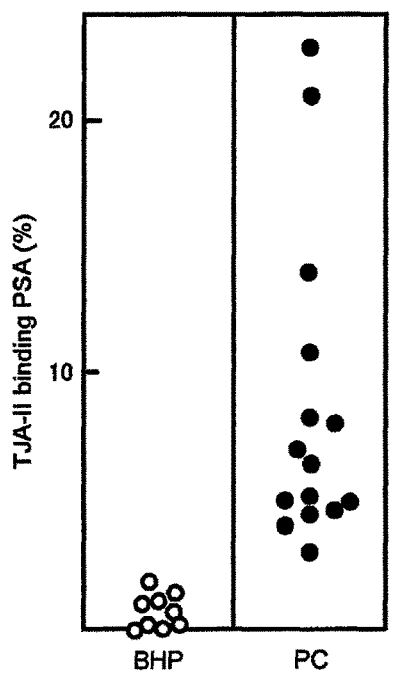
FIG. 3 is a graph showing an amount of PSA from a prostate cancer patient serum (PC: •) and the PSA from a prostatic hypertrophy patient serum (BHP: ○), in the TJA-II binding fractions.

As shown in FIG. 2 and FIG. 3, neither the amounts of TJA-II-bound PSA, nor the binding rates for TJA-II overlapped between the prostate cancer patients and the prostatic hypertrophy patients, which indicated that the prostate cancer patients can be distinguished from the prostatic hypertrophy patients. If the cutoff value of the TJA-II-bound PSA is assumed to be 250 pg/mL, and the cutoff value of the TJA-II binding rate tentatively to be 2%, the prostatic hypertrophy patients can be distinguished from the prostate cancer patients with 100% accuracy. In various clinical stages and Gleason scores, no significant difference was found in the TJA-II binding rate and the amount of TJA-II-bound PSA.

Example 2

In this example, the amount of PSA was measured by the method for analyzing PSA of the present invention for 3 patients diagnosed as having the prostate cancer using the WFA column prepared in the example of column preparation.

TABLE 1

| Sample | | PSA in serum sample (ng/mL) | TJA-II-bound PSA in serum sample (ng/mL) | TJA-II-unbound PSA in serum sample (ng/mL) | TJA-II binding ratio (%) | Free PSA/total PSA |
|---|---|---|---|---|---|---|
| Prostatic hypertrophy | 1 | 17.00 | 0.20 | 16.3 | 1.2 | 19.0 |
| | 2 | 10.40 | <0.005 | 10.1 | <0.05 | 5.0 |
| | 3 | 10.20 | 0.02 | 9.87 | 0.2 | 79.0 |
| | 4 | 6.80 | 0.04 | 6.56 | 0.6 | 76.0 |
| | 5 | 8.30 | 0.12 | 7.93 | 1.5 | 22.0 |
| | 6 | 9.60 | 0.17 | 9.14 | 1.8 | 7.0 |
| | 7 | 8.00 | <0.005 | 7.75 | <0.05 | 6.0 |
| | 8 | 9.20 | 0.09 | 8.83 | 1.0 | 16.0 |
| | 9 | 8.20 | <0.005 | 7.95 | <0.05 | 12.0 |
| Prostate cancer | 1 | 892.20 | 128.00 | 808.30 | 6.4 | 4.5 |
| | 2 | 101.00 | 6.60 | 92.92 | 5.0 | 11.9 |
| | 3 | 69.90 | 2.40 | 65.70 | 3.0 | 4.9 |
| | 4 | 944.80 | 9.50 | 873.95 | 4.5 | 16.8 |
| | 5 | 180.00 | 6.30 | 162.00 | 7.0 | 7.8 |
| | 6 | 3597.00 | 388.50 | 3100.60 | 10.8 | 3.9 |
| | 7 | 68.00 | 5.58 | 60.38 | 8.2 | 13.0 |
| | 8 | 4.30 | 0.90 | 3.27 | 21.0 | NT |
| | 9 | 6.00 | 0.84 | 4.98 | 14.0 | NT |
| | 10 | 10.00 | 0.46 | 9.24 | 4.6 | NT |
| | 11 | 4.50 | 1.04 | 3.32 | 23.0 | NT |
| | 12 | 53.80 | 4.30 | 47.88 | 8.0 | 17.0 |
| | 13 | 4.70 | 0.24 | 4.32 | 5.0 | 13.5 |
| | 14 | 21.20 | 0.85 | 19.71 | 4.0 | 10.0 |
| | 15 | 12.10 | 0.61 | 11.13 | 5.0 | 10.0 |

TABLE 2

| Sample | | Age | Clinical stage | Gleason score |
|---|---|---|---|---|
| Prostatic hypertrophy | 1 | 74 | — | — |
| | 2 | 75 | — | — |
| | 3 | 65 | — | — |
| | 4 | 70 | — | — |
| | 5 | 65 | — | — |
| | 6 | 52 | — | — |
| | 7 | 71 | — | — |
| | 8 | 71 | — | — |
| | 9 | 52 | — | — |
| Prostate cancer | 1 | 83 | 3c | 7 |
| | 2 | 77 | 3b | 9 |
| | 3 | 66 | 3b | 9 |
| | 4 | 64 | 3b | 9 |
| | 5 | 81 | 4 | 9 |
| | 6 | 81 | 3c | 7 |
| | 7 | 83 | 3b | 9 |
| | 8 | unknown | ND | ND |
| | 9 | unknown | ND | ND |
| | 10 | unknown | ND | ND |
| | 11 | unknown | ND | ND |
| | 12 | 74 | 3b | 9 |
| | 13 | 59 | 1c | 7 |
| | 14 | 64 | 1c | 7 |
| | 15 | 64 | 2a | 9 |

Specifically, the procedures of Example 1 were repeated except that the WFA column and an eluting buffer (PBS containing 10 mM GalNAc and 0.1% BSA) were used instead of the TJA-II column and the eluting solution (PBS containing 10 mM lactose and 0.1% BSA), and the serum samples of the 3 prostate cancer patients were analyzed, to obtain the amount of WFA-bound PSA and the WFA binding rate. The results of the WFA binding rate are shown in Table 3.

Meanwhile, the WFA binding rate was calculated by the following equation.

$$\text{WFA binding rate} = (\text{amount of } PSA \text{ in the } WFA \text{ binding fraction/total amount of } PSA \text{ in the } WFA \text{ non-binding fraction and in the } WFA \text{ binding fraction}) \times 100\%$$

In addition, the TJA-II binding rates are shown in Table 3 for comparison.

TABLE 3

| Sample | | PSA in serum sample (ng/mL) | WFA-bound PSA in serum sample (ng/mL) | WFA-unbound PSA in serum sample (ng/mL) | WFA binding ratio (%) | TJA-II binding ratio (%) |
|---|---|---|---|---|---|---|
| Prostate cancer | 6 | 3597.00 | 327.98 | 3161.11 | 9.4 | 10.8 |
| | 12 | 53.80 | 3.91 | 48.27 | 7.5 | 8.0 |
| | 15 | 12.10 | 0.49 | 11.50 | 4.2 | 5.0 |

The PSA recovery rate from the WFA column was 90% to 98%. In addition, the WFA binding rate was nearly correlated to the TJA-II binding rate, and WFA is bound to PSA having β-N-acetylgalactosamine residues, which makes it possible to separate PSA of the prostate cancer patient.

However, the percentage of the WFA binding rate to TJA-II binding rate was from 84.0% to 93.8%, which was somewhat lower than the TJA-II binding rate. This suggests the possibility that PSA having an affinity only for TJA-II exists in the blood of the prostate cancer patient. In other words, this suggests the possibility that PSA having only fucose α(1, 2) galactose residues (Fucα1→2Galβ1→R) but having no β-N-acetylgalactosamine residues (GalNAcβ1→R) exists.

Example 4

In this example, the binding rates of PSA to the TJA-II column, the UEA-I column and the WFA column were examined for PSA in the sera of the prostatic hypertrophy patients, PSA in the sera of the prostate cancer patients, and PSA in the seminal fluids of the normal person.

Measurement of the binding rate to the TJA-II column was performed in accordance with the method described in Example 1. Measurement of the binding rate to the WFA column was performed in accordance with the procedures described in Example 2.

In addition, measurement of the binding rate to the UEA-I column was performed as described below. The amount of UEA-I-bound PSA was measured using agarose immobilized with *Ulex europaeus* agglutinin-1 (UEA-I) (UEA-I agarose: J-oil mills). Specifically, the procedures of Example 1 were repeated except that UEA-I agarose and an eluting buffer (PBS containing 50 mM fucose and 0.1% BSA) were used instead of the TJA-II column and the eluting solution (PBS containing 10 mM lactose and 0.1% BSA), to measure the UEA-I binding rate. The results are shown in Table 4.

TABLE 4

| Lectin | Recognized sugar chain | PSA in serum of prostatic hypertrophy patient | PSA in serum of prostate cancer patient | PSA in seminal fluid |
|---|---|---|---|---|
| TJA-II | Fucα1→2Galβ1→4(3)GlcNAc and GalNAcβ1→ | 2.0% | 16% | 2% |
| UEA-I | Fucα1→2Galβ1→4GlcNAc | <1% | 5% | <1% |
| WFA | GalNAcβ1→ | <1% | 11% | <1% |

Little PSA in the serum of the prostatic hypertrophy patients is bound to the TJA-II column, the UEA-I column or the WFA column. On the other hand, for PSA in the sera of the prostate cancer patients, 16% PSA is bound to the TJA-II column, 5% PSA is bound to the UEA-I column, and 11% PSA is bound to the WFA column. These data show that PSA in the sera of the prostate cancer patients has β-N-acetylgalactosamine residues and fucose α(1, 2) galactose residues at the non-reducing terminal.

Comparative Example 1

In this Comparative Example, separation and measurement of PSA of prostate cancer patients were performed using MAA column, which is the lectin described in Patent Reference 1.

Purification of MAA was performed in accordance with the method previously reported (Kawaguchi et al., J. Biol. Chem., 249, 2786-2792, 1974). Concretely, 50 g of seeds of *Maackia amurensis* was homogenized finely with several hundred mL PBS by a homogenizer, stirred overnight, and then centrifuged at 9000 rpm for 30 minutes to exclude the precipitate. 50 to 80% ammonium sulfate fraction of this extract solution (210 mL) was dialyzed with PBS, and centrifuged to exclude the precipitate. Then, a portion (30 mL) of the resultant was added to thyroglobulin-Sepharose (19 mg/mL, 15 mL), washed with PBS, and then eluted with 0.15 M glycine hydrochloride buffer (pH 2.5) containing 0.1 M lactose and 0.075 M NaCl. Portions having high lectin activity were pooled, concentrated, and then dialyzed with 50 mM phosphate buffer (pH 4.5) for substitution. The precipitate was removed with the centrifuge procedure, and then the resultant was added to SP-Sephadex C-50 (100 mL) that was equilibrated with 50 mM phosphate buffer (pH 4.5), and the non-adsorbed fractions were collected and concentrated, to obtain purified MAA.

The MAA-Sepharose column was prepared using the purified MAA. The MAA column was prepared using CNBr-Sepharose (manufactured by GE HealthCare) by immobilizing MAA to the column in the concentration of 3 mg per 1 mL gel volume according to the enclosed protocol recommended by the manufacturer.

In order to check the binding property for a sialic acid α(2, 3) galactose residue of the MAA column, the binding was checked using a oligosaccharide having 3 sialic acid α(2, 3) galactose residues. At a temperature of 4° C., the MAA column (1 mL volume) was equilibrated with a phosphate buffer containing 0.1% bovine serum albumin (BSA) and 0.02% Tween. A tri-antennary oligosaccharide having 3 sialic acid α(2, 3) galactose residues was applied to the column, and held for 30 minutes. Then, the column was washed with a 5-fold volume of a washing buffer (phosphate buffer containing 0.1% BSA and 0.02% Tween), and fractionated to 1 mL for each to obtain the MAA non-bound molecules. Sequentially, the column was stood at room temperature, and then fractionated to 1 mL for each fraction and eluted with a 5-fold volume of an eluting buffer (phosphate buffer containing 400 mM lactose, 0.1% BSA and 0.02% Tween), to obtain the MAA bound molecules. The oligosaccharide having 3 sialic acid α(2, 3) galactose residues was weakly interacted with MAA-Sepharose column and 95% thereof were recovered with a washing buffer.

Figure 4:
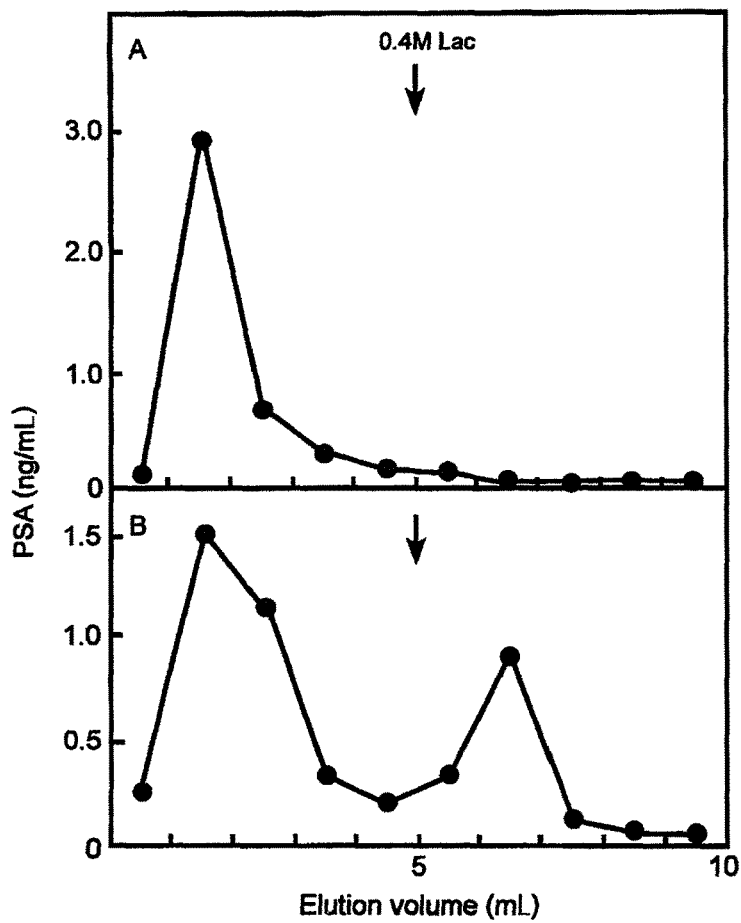
FIG. 4 is a graph showing the results of MAA column chromatography. PSA from normal seminal fluid (A) and PSA from prostate cancer patient serum (B) were fractionated by using an MAA column, followed by measuring an amount of free PSA.

Next, using this MAA column, the binding of PSA of a prostate cancer patient to the MAA column was examined. The MAA column (1 mL volume) was equilibrated with PBS containing 0.1% bovine serum albumin (BSA) and 0.02% Tween at 4° C. 10 μL of the serum sample was diluted with PBS to the volume of 200 μL, applied to the column, and held for 30 minutes. Then, the column was washed with 5-fold volume of a washing buffer (PBS containing 0.1% BSA and 0.02% Tween), and fractionated to 1 mL for each fraction to obtain five MAA non-binding fractions. The column was stood at room temperature, and then fractionated to 1 mL for each fraction and eluted with a 5-fold volume of an eluting buffer (PBS containing 400 mM lactose, 0.1% BSA and 0.02% Tween), to obtain five MAA binding fractions. For each of the fractions, the total PSA amount was measured using Access Hybritech total PSA (manufactured by Beckman Coulter Inc.). For control, the same procedures were repeated using 5 ng of purified PSA from normal seminal fluid, and the total amount of PSA was measured. The results of PSA of the prostate cancer patients are shown in FIG. 4(B), and the results of PSA from normal seminal fluid are shown in FIG. 4(A).

Most of PSA from normal seminal fluid was detected in the second MAA non-binding fraction. However, the total amount of the PSA in all fractions, was 3.5 ng, relative to 5 ng of normal PSA that was applied to the MAA column. Therefore, the recovery rate was 70%, and 30% was considered to be as bound to the column.

On the other hand, PSA of the prostate cancer patients is divided into the non-bound PSA detected in the second MAA non-binding fraction, the slightly bound PSA detected in the shoulder portion of the third MAA non-binding fraction, and the bound PSA eluted with 400 mM lactose. The total of the PSA amount in all the fractions was 4 ng/mL, relative to 10 ng/mL that was the amount of PSA in the serum sample before a separation. Thus, only about 40% of the amount of PSA before separation was recovered. This recovery rate did not improve even with use of 0.1 M acetic acid solution as the eluting solution. Furthermore, as for the used PSA of the prostate cancer patient, the ratio of free PSA/total PSA was 3.6, and 96.4% PSA existed in the form of PSA-ACT that was bound to α-antichymotrypsin. Since α-antichymotrypsin has one sialic acid α(2, 3) galactose residue per one molecule, PSA-ACT was anticipated to be bound to the MAA column. However, much of PSA was detected as the non-adsorbed PSA that was detected in the second MAA non-binding fraction, and as the slightly adsorbed PSA that was detected in the shoulder portion of the third MAA non-binding fraction.

In other words, the result that the oligosaccharide having 3 sialic acid α(2, 3) galactose residues is weakly interacted with the MAA column, and the result that some of PSA-ACT is not bound, show that the binding of PSA to the MAA lectin column is weak. In addition, although the binding of PSA to MAA is weak, it was considered that the recovery rate of PSA from MAA column was poor, that elution with the haptenic sugar was incomplete, and that measurement by MAA with good reproducibility and high accuracy was difficult.

INDUSTRIAL APPLICABILITY

With the method for analyzing PSA and the analysis kit of PSA of the present invention, it is possible to distinguish definitely between prostate cancer patients and prostatic hypertrophy patients. Accordingly, it is possible to find the prostate cancer in the early stage in a health examination. In addition, because it is possible to distinguish definitely between the prostate cancer and the prostatic hypertrophy, subjects for needing prostatic biopsy for confirmed diagnosis can be reduced, which can reduce the burden of patients.

Although the present invention has been described with reference to specific embodiments, various changes and modifications obvious to those skilled in the art are possible without departing from the scope of the appended claims.

The invention claimed is:

1. A method for analyzing PSA with a β-N-acetylgalactosamine residue, comprising the following step of:
  bringing into contact *Wisteria floribunda* agglutinin with a sample, which sample is a member selected from the group consisting of blood, serum, and plasma possibly containing PSA, wherein the amount of PSA is determined by measuring total PSA or free PSA, to determine an amount of PSA having an affinity for *Wisteria floribunda* agglutinin.

2. The method for analyzing PSA with a β-N-acetylgalactosamine residue according to claim 1, wherein the amount of PSA having an affinity for *Wisteria floribunda* agglutinin is determined
  (1) by measuring an amount of separated PSA having an affinity for *Wisteria floribunda* agglutinin,
  (2) by measuring an amount of PSA in a sample before the separation and an amount of the separated PSA having an affinity for *Wisteria floribunda* agglutinin, or
  (3) by measuring an amount of PSA in a sample, which sample is a member selected from the group consisting of blood, serum and plasma before the separation and an amount of the separated PSA lacking an affinity for *Wisteria floribunda* agglutinin.

3. The method for analyzing PSA with a β-N-acetylgalactosamine residue according to claim 1, wherein the sample, which sample is a member selected from the group consisting of blood, serum, and plasma, is obtained from a patient suspected of having prostate cancer.

4. A method for analyzing PSA having a β-N acetylgalactosamine residue, the method comprising:
  contacting a sample with *Wisteria floribunda* agglutinin, wherein the sample is a member selected from the group consisting of blood, serum, and plasma possibly containing PSA; and
  determining an amount of PSA having an affinity for *Wisteria floribunda* agglutinin, wherein the amount of PSA having an affinity for *Wisteria floribunda* agglutinin is greater for PSA associated with prostate cancer than non-prostate cancer PSA.

* * * * *